United States Patent [19]

Baines et al.

[11] Patent Number: 5,026,542
[45] Date of Patent: Jun. 25, 1991

[54] DEPILATORY COMPOSITION

[75] Inventors: Frederick C. Baines, Dunstable; Richard Johnston, Reading, both of England

[73] Assignee: The Gillette Company, Boston, Mass.

[21] Appl. No.: 414,156

[22] Filed: Sep. 28, 1989

[51] Int. Cl.$^5$ .................... A61K 7/15; A61K 7/155
[52] U.S. Cl. ........................... 424/73; 424/70; 424/71; 424/72; 424/78; 8/94.16; 8/160; 8/161
[58] Field of Search ............. 424/72, 73, 658; 8/94.16, 160, 161

[56] References Cited

FOREIGN PATENT DOCUMENTS 0196896 10/1986 European Pat. Off. .
61-282311 12/1986 Japan .

*Primary Examiner*—Thurman K. Page
*Assistant Examiner*—James M. Spear
*Attorney, Agent, or Firm*—Mandel E. Slater

[57] ABSTRACT

A two part depilatory composition in which the first part comprises polyvinyl alcohol and the second part comprises a cross-linking agent which consists of borax and a polyhydroxy alcohol or of Congo red, the first or second or both parts additionally containing a depilatory agent, the two parts containing such proportions of the ingredients specified that when the parts are mixed in such proportions that there is sufficient borax or Congo red to effect cross-linking of the polyvinyl alcohol, the mixed composition contains sufficient depilatory agent to effect depilation in an acceptable period and, when the second part comprises borax, sufficient polyhydroxy alcohol to moderate the rate of cross-linking.

6 Claims, No Drawings

DEPILATORY COMPOSITION

This invention is concerned with depilatory compositions.

The currently available depilatory compositions generally consist of a depilatory agent in a cream base. The most commonly used depilatory agent is calcium thioglycollate, but a number of other such agents are known, such as other salts of thioglycollic acid, for example the sodium, potassium and lithium salts, the sulphides of alkali and alkaline earth metals and thiols, such as thioglycerol. In use, the composition is applied as a relatively thick coating, say up to 2 mm thick, to the area where it is wished to remove hair, such as the legs or the axilla, and is left in situ for a sufficient length of time, say up to 10 minutes, for the hair to be chemically dissolved. The cream base should, of course, be formulated so as to have a sufficiently high viscosity that the composition does not flow away from the area to which it has been applied.

After the necessary treatment period, the cream and hair debris are wiped or washed off the skin; the skin should be thoroughly washed since most depilatory creams have a high pH and may give rise to irritation if not completely removed from the skin.

The operation of removing the cream and hair debris is tedious and disliked by some users. With a view to improving this aspect of the use of depilatory compositions, it has been proposed, European Specification No. 0196896A, that the composition should be based on a solution of a film-forming polymer from which the solvent, such as water, is removed by natural or accelerated drying during the treatment period to form a peelable coherent coating. At the end of the treatment period the coating is simply peeled off the treated skin area taking the hair debris with it.

A generally similar prior proposal is made in Japanese Patent Publication No. 61-282311 which describes a two part depilatory composition, one part of which comprises a solution of a polymer or polymer-forming compound and the other part of which contains a component that reacts with the polymer or polymer-forming compound to form a solidified peelable coating, the depilatory agent being contained in one or other or both of the parts. The Japanese specification mentions polyacrylic acids and salts thereof, polyacrylamides, cellulose esters, alginic acid and salts thereof as examples of suitable polymers for use in the first part of such compositions. Suitable reactive components for the second part depend, of course, on the nature of the polymeric component in the first part and include, for example, metal salts that form cross-links with the polymeric component, compounds that bring about acid or base reactions with the polymeric component, and compounds that react with reactive groups present in the polymeric component.

The Japanese specification describes the two parts of the composition being applied to the treatment area separately, that is one after the other.

We have now developed a two part depilatory composition based on a particularly well tolerated polymeric material, that is polyvinyl alcohol. It is known that polyvinyl alcohol can be cross-linked under alkaline conditions by borax, but the cross-linking reaction is so rapid that the polyvinyl alcohol/borax system can not, in practice, be used in a two part depilatory composition as the composition solidifies too quickly, that is to say there would not be sufficient time to mix the components thoroughly and spread the mixture over the area to be depilated.

The present invention is based, therefore, not only on the choice of the polyvinyl alcohol/borax system as the basis of a two part depilatory composition, but on the discovery that the rate of cross-linking in this system can be controlled, that is reduced, by the presence of a polyhydroxy alcohol.

The present invention is also based on the knowledge that polyvinyl alcohol can be cross-linked by the compound Congo red, the chemical name of which is sodium diphenyldiazo-bis-α-naphthylamine-sulphonate; Congo red is a well known acid/alkali indicator. The cross-linking reaction with Congo red is not so fast as that with borax and it is not necessary to use a moderating compound, such as the polyhydroxy compound used with borax.

According to the present invention, there is provided a two part depilatory composition in which the first part comprises polyvinyl alcohol and the second part comprises a cross-linking agent which consists of borax and a polyhydroxy alcohol or of Congo red, the first or second or both parts additionally containing a depilatory agent, the two parts containing such proportions of the ingredients specified that when the parts are mixed in such proportions that there is sufficient borax or Congo red to effect cross-linking of the polyvinyl alcohol, the mixed composition contains sufficient depilatory agent to effect depilation in an acceptable period and, when the second part comprises borax, sufficient polyhydroxy alcohol to moderate the rate of cross-linking.

Suitably polyhydroxy alcohols for use in conjunction with borax have a 1,2- or 1,3-diol structure in a favourable stereochemical configuration; such alcohols include glycerol, mannitol, glucose, fructose, sucrose, propane-1,2-diol, and 2,4-pentane-diol, of which the first, glycerol, is preferred.

It is preferred to use the composition according to the invention by mixing the two parts and applying the mixed composition to the area to be treated. The proportions of the active ingredients in the two parts are preferably such that optimum proportions of polyvinyl alcohol: borax: polyhydroxy alcohol or polyvinyl alcohol: Congo red and of depilatory agent are obtained by mixing from 30 to 70 parts by weight of the first part with from 70 to 30 parts by weight of the second part and, more preferably, by mixing equal parts by weight of the two parts. The optimum proportions referred to are those which give dissolution of the hair and solidification of the composition in less than 10 minutes.

It will be understood that as with conventional depilatories, the two parts should be formulated so as to have viscosities such that, on the one hand, they can be readily mixed and, on the other, the mixture will not flow away from the treated area to any significant extent. The rheological properties of the first and second parts of the composition can be modified by the use of fillers, such as talc, calcium carbonate and fibrous materials.

The first part of the composition is preferably an aqueous dispersion or solution containing 10 to 25%, more preferably 16%, by weight of polyvinyl alcohol. Various grades of the latter can be used and the choice of grade is not critical; 88% hydrolysed polyvinyl alcohol having a molecular weight of about 125,000 is, for example, suitable.

The first part preferably additionally comprises one or more non-ionic or anionic surfactants and also preservatives and perfumes such as are conventionally included in cosmetic compositions.

The second part of the composition preferably comprises the other active ingredients, that is the depilatory agent, the borax and the polyhydroxy alcohol or the Congo red.

The preferred depilatory agent is calcium thioglycollate, preferably used as the trihydrate, but as indicated above other depilatory agents are known and they can be used in the composition of this invention.

The second part of the composition is preferably an aqueous dispersion containing 6 to 20%, more preferably 18%, by weight of calcium thioglycollate trihydrate, and either 0.01 to 0.07%, more preferably 0.04%, by weight of borax, and 0.05 to 10%, more preferably 2%, by weight of glycerol, or 0.5 to 5%, more preferably 1 to 2%, by weight of Congo red. Calcium thioglycollate requires a relatively high pH in order to be an effective depilatory agent and the second part, therefore, further comprises one or more bases, such as caustic soda and calcium hydroxide, so that it has a pH of from 10.5 to 12.5.

The second part preferably further comprises one or more non-ionic surfactants and also preservatives and perfumes such as are conventionally included in cosmetic preparations.

In order that the invention may be more fully understood, the following examples, in which all parts and percentages are by weight, are given by way of illustration only:

EXAMPLE 1

A two part depilatory of the following composition was prepared:

|  | parts |
|---|---|
| Part 1 | |
| polyvinyl alcohol (88% hydrolysed), MW 125,000) | 8 |
| polyoxyethylene (10)nonyl phenyl ether (Nonoxynol-10, Trade Mark) | 1 |
| perfume | 0.05 |
| methyl chloroisothiazolinone plus methyl isothiazolinone (preservative), Kathon CG (Trade Mark) | 0.02 |
| water | 40.93 |
|  | 50.00 |
| Part 2 | |
| calcium thioglycollate, 3H$_2$O | 9 |
| calcium hydroxide | 4 |
| sodium hydroxide 8N solution | 3 |
| glycerol | 1 |
| borax (as 1% aqueous solution) | 2 |
| steareth-21 (Brij 721) | 1 |
| steareth-2 (Brij 72) | 3 |
| stearyl alcohol | 2.5 |
| perfume | 0.125 |
| water | 24.375 |
|  | 50.00 |

Both parts have viscosities such that they can be easily mixed and do not flow away when applied to the area to be depilated.

Equal amounts by weight of the two parts were placed on a dish, mixed manually with a spatula and the mixed composition was applied as an approximately 2 mm coating to a hairy portion of the forearm of a male volunteer. There was no significant flow of the mixed composition from the site of application.

After 10 minutes, the composition had solidified to a pliable, rubber-like consistency. The solidified composition was peeled off the treated area and was observed to have hair debris embedded in it. The treated area of skin was hairless.

EXAMPLES 2 AND 3

Two two-part depilatories were prepared. For each the formulation of Part 1 was as described in Example 1; the formulations of part 2 differed as to amount of Congo red present, the Part 2 formulation of Example 2 containing 1.0% and that of Example 3 containing 2.0% of Congo red. The formulations were as follows:

| Part 2 | Ex. 2 parts | Ex. 3 parts |
|---|---|---|
| calcium thioglycollate, 3H$_2$O | 9 | 9 |
| calcium hydroxide | 4 | 4 |
| steareth-2 (Brij 72) | 3 | 3 |
| steareth-21 (Brij 721) | 1 | 1 |
| stearyl alcohol | 2.5 | 2.5 |
| Congo red | 0.5 | 1.0 |
| water | 27.0 | 26.5 |
|  | 50.0 | 50.0 |

These two formulations of Part 2 had viscosities such that they could be easily mixed and did not flow away when applied to the area to be depilated.

Equal amounts by weight of Part 1 and Part 2 were mixed, the mixture including the Part 2 composition of Example 2 being mixed for one minute and that including the Part 2 composition of Example 3 for thirty seconds, and the mixture was applied to the area to be depilated. The mixtures solidified, due to cross-linking of the polyvinyl alcohol, in about five minutes and after ten minutes could be peeled from the skin to give very good depilation.

We claim:

1. A two part depilatory composition in which the first part comprises 10 to 25 percent by weight of polyvinyl alcohol and the second part comprises a cross-linking agent selected from the class consisting of (a) borax and a polyhydroxy alcohol and (b) Congo red, said depilatory composition further comprising 6 to 20 percent by weight of a depilatory agent in at least one of said first and second parts, the two parts containing such proportions said first part having from 30 to 70 parts by weight and said second part having from 70 to 30 parts by weight of the ingredients specified that when the parts are mixed in such proportions that there is sufficient borax or Congo red to effect cross-linking of the polyvinyl alcohol, the mixed composition contains sufficient depilatory agent to effect depilation in an acceptable period and, when the second part comprises borax, sufficient polyhydroxy alcohol to moderate the rate of cross-linking.

2. A two part composition according to claim 1, in which the first part is an aqueous dispersion or solution.

3. A two part composition according to claim 2, in which the first part additionally contains one or more non-ionic or anionic surfactants.

4. A two part composition according to claim 2, in which the second part is an aqueous dispersion containing 6 to 20% by weight of calcium thioglycollate trihydrate as the depilatory agent, and either 0.01 to 0.07% by weight of borax and 0.5 to 10% by weight of the polyhydroxy alcohol, or 0.5 to 5% by weight of Congo red, and sufficient base so that the second part has a pH of from 10.5 to 12.5.

5. A two part composition according to claim 4, in which the polyhydroxy alcohol is glycerol.

6. A two part composition according to claim 4, in which the second part additionally contains one or more non-ionic surfactants.

* * * * *